United States Patent
Sasaki et al.

Patent Number: 4,764,636
Date of Patent: Aug. 16, 1988

[54] OPTICALLY ACTIVE BENZOIC ESTER DERIVATIVES

[75] Inventors: Makoto Sasaki, Urawa; Kiyohumi Takeuchi, Tokyo; Haruyoshi Takatsu, Kodaira, all of Japan

[73] Assignee: Dainippon Ink and Chemicals, Inc., Tokyo, Japan

[21] Appl. No.: 926,706

[22] Filed: Oct. 31, 1986

[30] Foreign Application Priority Data

Nov. 1, 1985 [JP] Japan ................... 60-245766

[51] Int. Cl.$^4$ ............................. C07C 69/76
[52] U.S. Cl. ........................... 560/102; 544/296; 544/335
[58] Field of Search ............ 560/102; 544/296, 335

[56] References Cited
FOREIGN PATENT DOCUMENTS

A0110299 6/1984 European Pat. Off.
3317597 11/1984 Fed. Rep. of Germany.

*Primary Examiner*—Paul J. Killos
*Attorney, Agent, or Firm*—Armstrong, Nikaido, Marmelstein & Kubovcik

[57] ABSTRACT

An optically active benzoic ester derivative represented by the general formula:

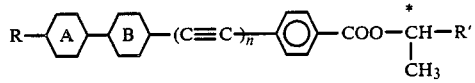

wherein R represents a straight chain alkyl group having from 1 to 20 carbon atoms; R' represents a straight chain alkyl group having from 2 to 8 carbon atoms; rings A and B each represents

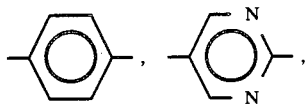

or a trans-1,4-cyclohexane ring; n represents 0 or 1; and $\overset{*}{C}$ represents an asymmetric carbon atoms. The compounds of formula (I) are capable of providing a chiral nematic liquid crystal composition having a short spiral pitch when added to a nematic liquid crystal composition in a small amount and are useful in the production of SBE display devices having excellent performances in a high level multiplexing driving system.

5 Claims, 1 Drawing Sheet

OPTICALLY ACTIVE BENZOIC ESTER DERIVATIVES

FIELD OF THE INVENTION

This invention relates to a novel optically active benzoic ester derivative useful as an electrooptical display material.

BACKGROUND OF THE INVENTION

In TN (twisted nematic) type liquid crystal devices, prevention of generation of reverse domain is usually achieved, at present, by adding about 0.1% of a cholesteric liquid crystal or about 0.1 to 1% of an optically active compound to a nematic liquid crystal composition.

The SBE (supertwisted birefringence effect) display device recently proposed by T. J. Scheffer et al., *Applied Physics Letters*, Vol. 45, 1021–1023 (1984) is excellent especially in high level multiplexing driving system and is suitable for a flat panel. The nematic liquid crystals in the SBE display device are twisted at an angle of 180° to 270° by addition of an optically active compound. Therefore, it has been demanded to develop an optically active compound which can afford a short spiral pitch when added in an amount as small as possible.

SUMMARY OF THE INVENTION

One object of this invention is to provide a novel optically active compound which can form a chiral nematic liquid crystal composition having a short spiral pitch by adding a small amount thereof to a nematic liquid crystal composition.

The above object of this invention can be accomplished by a compound represented by the general formula:

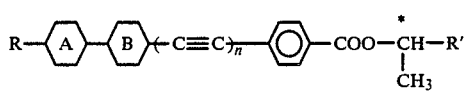   (I)

wherein R represents a straight chain alkyl group having from 1 to 20 carbon atoms; R' represents a straight chain alkyl group having from 2 to 8 carbon atoms; rings A and B each represents

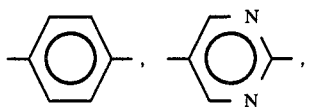

or a trans-1,4-cyclohexane ring; n represents 0 or 1; and C represents an assymmetric carbon atom.

BRIEF DESCRIPTION OF THE ACCOMPANYING DRAWING

FIG. 1 is a graph showing a relationship between the amount of the compounds of the present invention (Compound Nos. 1 to 4) which shows in weight percent based on the total weight and the reciprocal (1/P) of the spiral pitch (P) of the liquid crystals obtained when the compounds of this invention are added in varying proportions to the host liquid crystal (A) which is now widely used as a nematic liquid crystal material.

DETAILED DESCRIPTION OF THE INVENTION

Figure 1:
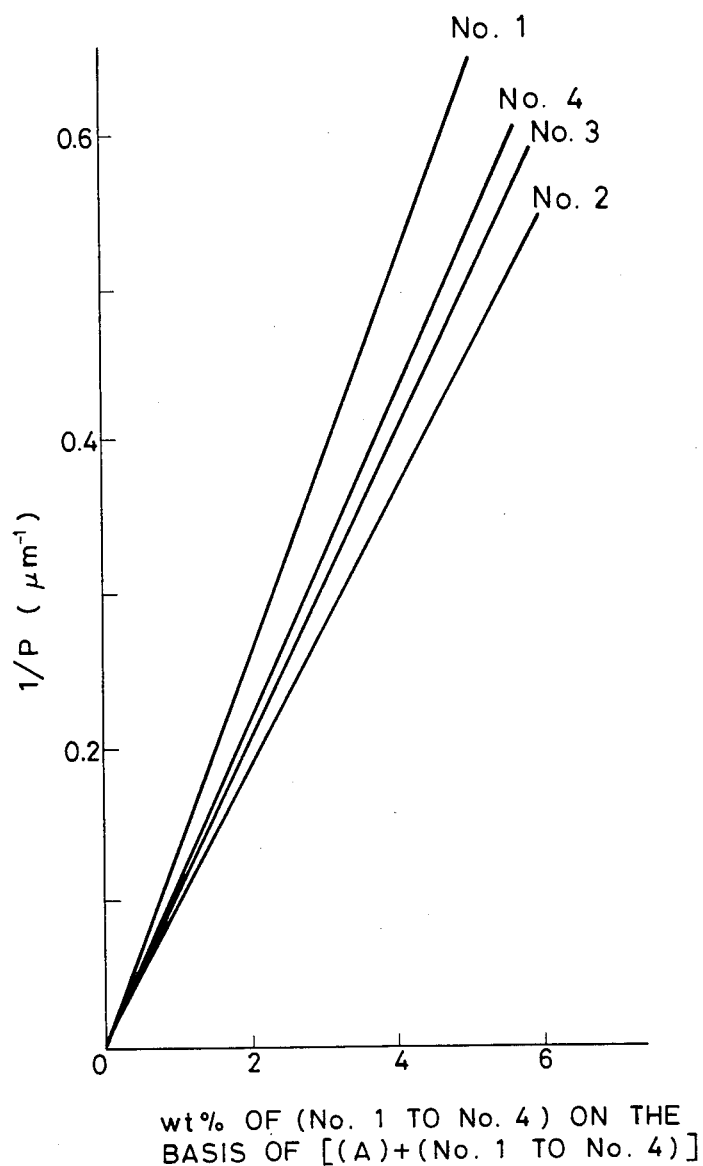

The compounds of formula (I) according to the present invention can be synthesized by the following reaction scheme:

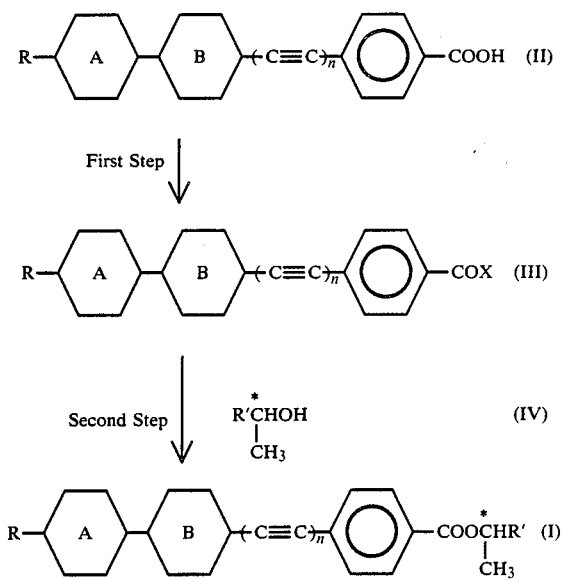

wherein R, R', A, B and $\overset{*}{C}$ are as defined above; and X represents a halogen atom.

In the first step, a compound of formula (II) is reacted with a halogenating agent to prepare a compound of formula (III). In the compound of formula (III), X preferably represents a chlorine atom, and a preferred halogenating agent is thionyl chloride. The reaction is carried out at a refluxing temperature under atmospheric pressure. After completion of the reaction, the excess halogenating agent is removed from the reaction mixture. The produced compound of formula (III) needs not be isolated from the reaction mixture.

In the second step, the crude compound (III) as prepared in the first step is reacted with an optically active alcohol of formula (IV) in a basic solvent, such as pyridine. The reaction mixture is subjected to purification procedures, such as solvent extraction, washing with water, drying, recrystallization, and the like, to isolate the desired compound of formula (I).

The transition temperature and optical rotation of the typical compounds of formula (I) thus prepared are shown in Table 1 below.

TABLE 1

$$R-\overset{A}{\bigcirc}-\overset{B}{\bigcirc}-(C\equiv C)_n-\bigcirc-COO\overset{*}{C}H-R'$$
$$\qquad\qquad\qquad\qquad\qquad\qquad\qquad |$$
$$\qquad\qquad\qquad\qquad\qquad\qquad\qquad CH_3$$

| Compound No. | R | -A- -B- | n | R' | Transition Temperature (°C.) | Optical Rotation $[\alpha]_D^{25}$ |
|---|---|---|---|---|---|---|
| 1 | n-$C_5H_{11}$— | -H- -◯- | 0 | n-$C_6H_{13}$— | 90 (S* ⇌ I**) | −32.1 |
| 2 | n-$C_3H_7$— | -H- -◯- | 1 | n-$C_6H_{13}$— | 55 (S ⇌ I) | −30.5 |
| 3 | n-$C_5H_{11}$— | -H- -◯(N,N)- | 0 | n-$C_6H_{13}$— | 91 (C*** → I) | −27.1 |
| 4 | n-$C_4H_9$— | -◯- -◯(N,N)- | 0 | n-$C_6H_{13}$— | 120 (S ⇌ I) | −34.7 |

Note:
*: S represents a smectic phase.
**: I represents an isotropic liquid phase.
***: C represents a crystalline phase. (hereinafter the same)

The compounds of formula (I) according to this invention can be used in admixture with nematic liquid crystal compositions commonly employed as electro-optical display materials. Preferred examples of liquid crystal compounds which can be used in admixture with the compounds of formula (I) include 4-substituted phenyl 4'-substituted benzoates, 4-substituted phenyl 4'-substituted cyclohexanecarboxylates, 4-substituted biphenyl 4'-substituted cyclohexanecarboxylates, 4-substituted phenyl 4'-(4"-substituted cyclohexanecarbonyloxy)benzoates, 4-substituted phenyl 4'-(4"-substituted cyclohexyl)benzoates, 4-substituted cyclohexyl 4'-(4"-substituted cyclohexyl)benzoates, 4-substituted 4'-substituted biphenyls, 4-substituted phenyl 4'-substituted cyclohexanes, 4-substituted 4'-substituted terphenyls, 4-substituted biphenyl 4'-substituted cyclohexanes, and 2-(4'-substituted phenyl)-5-substituted pyrimidiens, etc.

FIG. 1 illustrates a relationship between the amount of the compounds of the present invention (Compound Nos. 1 to 4) and the reciprocal (1/P) of the spiral pitch (P) of the liquid crystals obtained when these compounds are added in varying proportions to a host liquid crystal (A) which is now widely used as a nematic liquid crystal material. The host liquid crystal (A) comprises:

24% by weight of n-$C_3H_7$—-H--◯-CN,

36% by weight of n-$C_5H_{11}$—-H--◯-CN,

-continued

25% by weight of n-$C_7H_{15}$—-H--◯-CN, and

15% by weight of n-$C_5H_{11}$—-H--◯--◯-CN.

FIG. 1 clearly proves that addition of a small amount of the compound of the invention to a host nematic liquid crystal results in a nematic liquid crystal composition having a drastically increased 1/P value, i.e., a chiral nematic liquid crystal composition having a short spiral pitch.

This invention will now be illustrated in greater detail with reference to the following examples, but it should be understood that they are not intended to limit the present invention.

EXAMPLE 1

To 3.5 g (0.01 mol) of 4-(trans-4'-n-pentylcyclohexyl)biphenylcarboxylic acid was added excess thionyl chloride, and the mixture was heat-refluxed for 2 hours. After completion of the reaction, the excess thionyl chloride was removed by distillation under reduced pressure. To the residue were added 20 ml of pyridine and 1.3 g (0.01 mol) of (R)-(−)-2-octanol, followed by allowing the mixture to react at 50° C. for 1 hour. After the reaction, the reaction mixture was extracted with toluene under an acidic condition with hydrochloric acid, and the extract was washed with water, dried, and recrystallized from ethanol to give 2.8 g (0.006 mol) of the following compound:

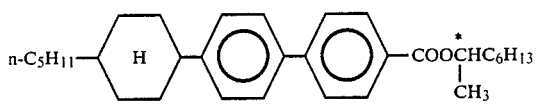

Yield: 60% $[\alpha]_D^{25} = -32.1°$ Transition Temperature: 90° C. (S⇌I)

EXAMPLE 2

The following compound was obtained in the same manner as in Example 1.

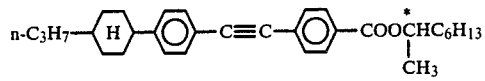

Yield: 52% $[\alpha]_D^{25} = -30.5°$ Transition Temperature: 55° C. (S⇌I)

EXAMPLE 3

The following compound was obtained in the same manner as in Example 1.

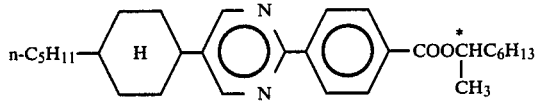

Yield: 64% $[\alpha]_D^{25} = -27.1°$ Transition Temperature: 91° C. (C→I)

EXAMPLE 4

The following compound was obtained in the same manner as in Example 1.

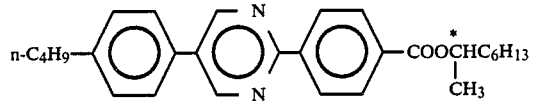

Yield: 67% $[\alpha]_D^{25} = -34.7°$ Transition Temperature: 120° C. (S⇌I)

As described above, the compounds in accordance with the present invention are capable of providing a chiral nematic liquid crystal composition having a short spiral pitch by adding a small amount thereof to an ordinary nematic liquid crystal composition. Thus, the compounds of the invention are effective in the production of SBE display devices having excellent performances in a high level multiplexing driving system.

While the invention has been described in detail and with reference to specific embodiments thereof, it will be apparent to one skilled in the art that various changes and modifications can be made therein without departing from the spirit and scope thereof.

What is claimed is:

1. An optically active benzoic ester derivative represented by the general formula:

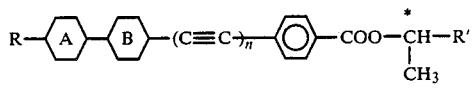

wherein R represents a straight chain alkyl group having from 1 to 20 carbon atoms; R' represents a straight chain alkyl group having from 2 to 8 carbon atoms; rings A and B each represents

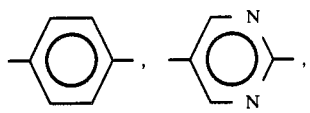

or a trans-1,4-cyclohexane ring; n represents 0 or 1; and $\overset{*}{C}$ represents an asymmetric carbon atom.

2. An optically active benzoic ester derivative of claim 1, wherein R is n—$C_5H_{11}$—, ring A is

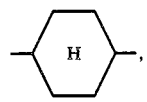

ring B is

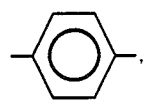

R' is n—$C_6H_{13}$—, and n is 0.

3. An optically active benzoic ester derivative of claim 1, wherein R is n—$C_3H_7$—, ring A is

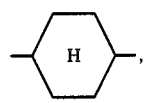

ring B is

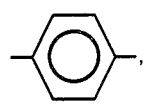

R' is n—$C_6H_{13}$—, and n is 1.

4. An optically active benzoic ester derivative of claim 1, wherein R is n—$C_5H_{11}$—, ring A is

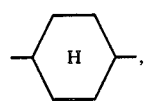

ring B is

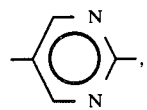

R' is n—$C_6H_{13}$—, and n is 0.

5. An optically active benzoic ester derivative of claim 1, wherein R is n—$C_4H_9$—, ring A is ring B is 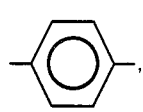
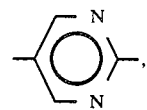 R′ is n—$C_6H_{13}$—, and n is 0.
* * * * *